(12) United States Patent
Barry (10) Patent No.: US 10,406,331 B2
(45) Date of Patent: Sep. 10, 2019

(54) DEVICE AND METHOD TO LOCATE AND READ AN IMPLANTED DEVICE USING ULTRASOUND

(71) Applicant: INTEGRA LIFESCIENCES SWITZERLAND SÀRL, Le Locle (CH)

(72) Inventor: Donald Barry, Franklin, MA (US)

(73) Assignee: INTEGRA LIFESCIENCES SWITZERLAND SÀRL, Le Locle (CH)

( * ) Notice: Subject to any disclaimer, the term of this patent is extended or adjusted under 35 U.S.C. 154(b) by 353 days.

(21) Appl. No.: 15/350,831

(22) Filed: Nov. 14, 2016

(65) Prior Publication Data

US 2018/0133444 A1 May 17, 2018

(51) Int. Cl.
*A61M 27/00* (2006.01)
*A61M 39/22* (2006.01)

(52) U.S. Cl.
CPC .......... *A61M 27/006* (2013.01); *A61M 39/22* (2013.01); *A61M 2039/226* (2013.01); *A61M 2205/3375* (2013.01); *A61M 2205/50* (2013.01); *A61M 2205/502* (2013.01); *A61M 2205/581* (2013.01); *A61M 2205/583* (2013.01)

(58) Field of Classification Search
CPC ................ A61M 27/006; A61M 39/22; A61M 2205/581; A61M 2205/583; A61M 2205/3375; A61M 2205/50; A61M 2039/226; A61M 2205/502

USPC .................................................. 600/437–469
See application file for complete search history.

(56) References Cited

U.S. PATENT DOCUMENTS

| | | | |
|---|---|---|---|
| 5,201,715 A | 4/1993 | Masters | |
| 5,383,466 A | 1/1995 | Partika | |
| 6,050,969 A * | 4/2000 | Kraus | A61M 27/006 600/12 |
| 6,740,076 B2 | 5/2004 | Hoben et al. | |
| 7,496,456 B2 | 2/2009 | Hiyama et al. | |
| 7,549,960 B2 | 6/2009 | Govari | |
| 8,617,079 B2 | 12/2013 | Mitchell | |
| 2005/0022403 A1* | 2/2005 | Moskowitz | A61M 27/006 33/355 R |
| 2005/0092335 A1* | 5/2005 | Bertrand | A61B 5/06 128/899 |
| 2005/0096579 A1* | 5/2005 | Bertrand | A61M 27/006 604/9 |
| 2007/0005000 A1* | 1/2007 | Ludin | A61M 27/006 604/9 |
| 2014/0276346 A1* | 9/2014 | Sadanand | A61M 27/006 604/9 |
| 2014/0336560 A1* | 11/2014 | Hakim | A61M 27/006 604/9 |
| 2018/0015266 A1* | 1/2018 | Amery | A61M 27/006 |
| 2018/0126147 A1* | 5/2018 | Hakim | A61M 27/006 |

\* cited by examiner

*Primary Examiner* — Sanjay Cattungal
(74) *Attorney, Agent, or Firm* — Troutman Sanders LLP (57) ABSTRACT

A subcutaneous implantable device has one or more adjustable settings with a setting device configured to selectively change between the one or more adjustable settings. An indicator, having an ultrasound reflection enhancement, indicates each particular setting of the one or more adjustable settings.

12 Claims, 7 Drawing Sheets

DEVICE AND METHOD TO LOCATE AND READ AN IMPLANTED DEVICE USING ULTRASOUND

FIELD OF THE INVENTION

The invention relates generally to surgically implantable fluid drainage systems. More specifically, the invention relates using ultrasound to locate the adjustable valves and their settings.

BACKGROUND

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain is blocked in some way. Such blockage can be caused by a number of factors, including, for example, genesetting predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the bloodstream. Typically, the shunt valve is palpatable by the physician through the patient's skin after implantation.

Shunt valves, which can have a variety of configurations, can be designed to allow adjustment of their fluid drainage characteristic after implantation. It is generally preferred to enable external adjustment of the pressure threshold to avoid invasive surgical procedures each time an adjustment is required. In some shunt systems, the shunt valve contains a magnetized rotor to control the pressure threshold of the valve. Physicians can then use an external adjustment mechanism, such as a magnetic programmer containing a powerful magnet, to adjust the pressure threshold of the shunt valve. One issue with magnetically programmable valves is a potential for unintentionally adjusting the valve by the misapplication of an external magnetic field. Unintentional adjustment of the valve could lead to either the overdrainage or underdrainage of CSF, which can result in dangerous conditions, such as subdural hematoma. Thus, the setting position for adjustable CFS or hydrocephalus shunt valves must be verified after adjustment, or, after exposure to strong magnetic fields such as MRI.

Known methods to externally read or verify the setting of the valve can be burdensome or inaccurate. With some adjustable valves, x-ray images are used to determine the current setting of the valve, before and after adjustment, which is very burdensome. With other adjustable valves, the orientation of the rotor in the valve can be read magnetically, using a magnetic compass-like device positioned above the valve, outside the skin of the patient. However, these can be inaccurate because they can be interfered with by extraneous magnetic fields caused by Earth or local devices.

Thus, a need exists for an easier and more reliable way to verify the position of the valve's settings.

SUMMARY

The present invention includes examples of a subcutaneous implantable device having one or more adjustable settings. This includes a setting device configured to selectively change between the one or more adjustable settings, and an indicator indicating each particular setting of the one or more adjustable settings and comprising an ultrasound reflection enhancement. In other examples, the subcutaneous implant can have the indicator as part of the setting device. Alternately, the indicator can further have one or more setting marks, each mark identifying each particular setting of the one or more adjustable settings, an identifier identifying each mark as set by the setting device, and the one or more setting marks and the identifier comprise the ultrasound reflection enhancement.

Another example of the subcutaneous implantable can include an orientation axis determining a positional orientation of the device as implanted, an axis identifier disposed along at least a portion of the orientation axis and comprising an ultrasound reflection enhancement, and the indicator indicates the particular settings in relation to the axis identifier. Further, examples have a body, enclosing at least the setting device, a perimeter outlining the body, an outline mark along at least a portion of the perimeter and comprising an ultrasound reflection enhancement, and the indicator indicates the particular settings in relation to the outline mark. The body can be asymmetric.

An example of an adjustment tool for a subcutaneous implantable device having one or more adjustable settings has an adjusting tool configured to change the one or more adjustable settings, an ultrasound probe configured with the adjusting tool to take real-time readings of the one or more adjustable settings as the adjustment tool makes the change, and a display linked to the probe and indicating the setting. The adjustment tool can also be in a kit with a subcutaneous implantable device having one or more adjustable settings. The implant can have a setting device configured to selectively change between the one or more adjustable settings; and an indicator indicating each particular setting of the one or more adjustable settings and comprising an ultrasound reflection enhancement. The adjustment tool can also have the indicator with one or more setting marks, each mark identifying each particular setting of the one or more adjustable settings, an identifier identifying each mark as set by the setting device, and the one or more setting marks and the identifier comprise the ultrasound reflection enhancement.

Other examples of methods to determine a setting of a subcutaneous implantable device having one or more adjustable settings can be disposing an ultrasound probe proximate the subcutaneous implantable device, reading an indicator indicating the setting of the one or more adjustable settings based on an ultrasound reflection enhancement on the indicator, and displaying the setting. The method can also include changing the one or more adjustable settings using a adjusting tool, and the reading and displaying steps are performed contemporaneous with the changing step.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Figure 1:
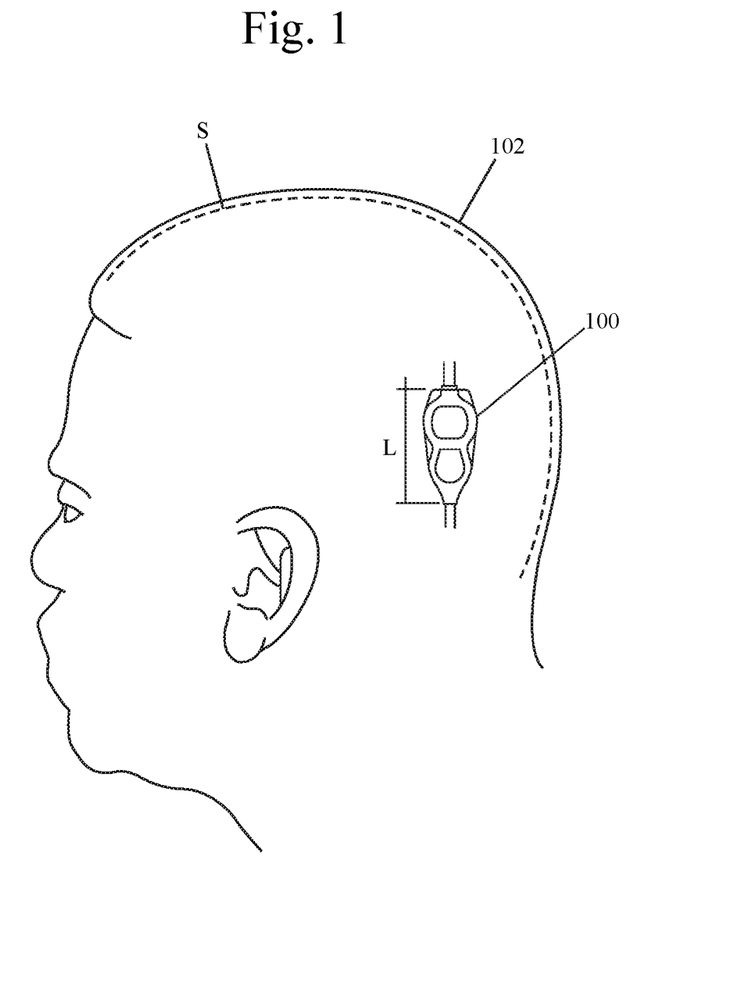
FIG. 1 is an illustration of the valve implanted in a patient.

FIG. 1 illustrates a generalized implantable device 100 with typically two or more settings. In the below examples, an implantable shunt valve is described, but any adjustable subcutaneous implanted device can be improved using examples of the invention. In examples, the valve 100 is implanted under the skin 102 of a patient's skull S. The valve 100 can have a long axis L along which the fluid flows. Once implanted, the valve is under the skin and typically covered by hair. Additionally, the area surrounding the valve may experience localized swelling, especially after surgery.

Figure 2A:
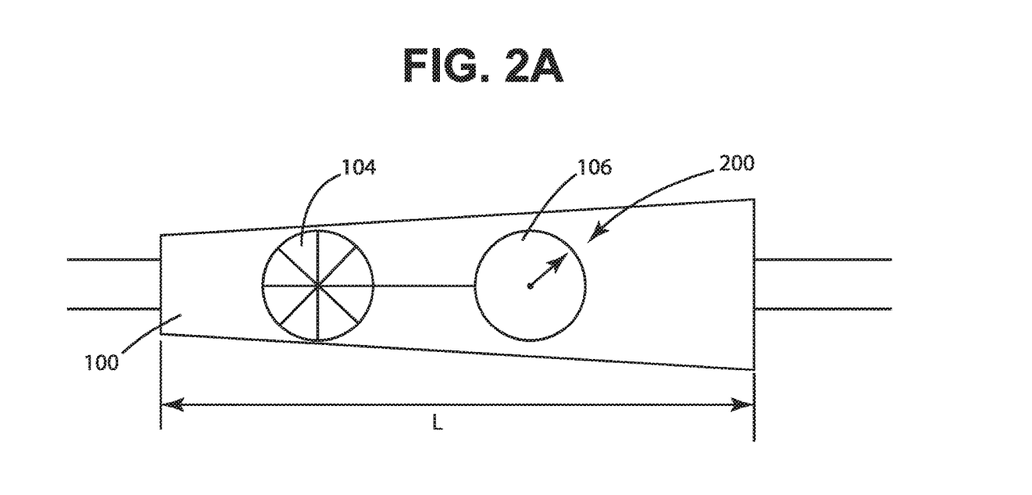
FIGS. 2A and 2B are top and side sections views, respectively, of an example of an implantable valve of the present invention.
Figure 2B:
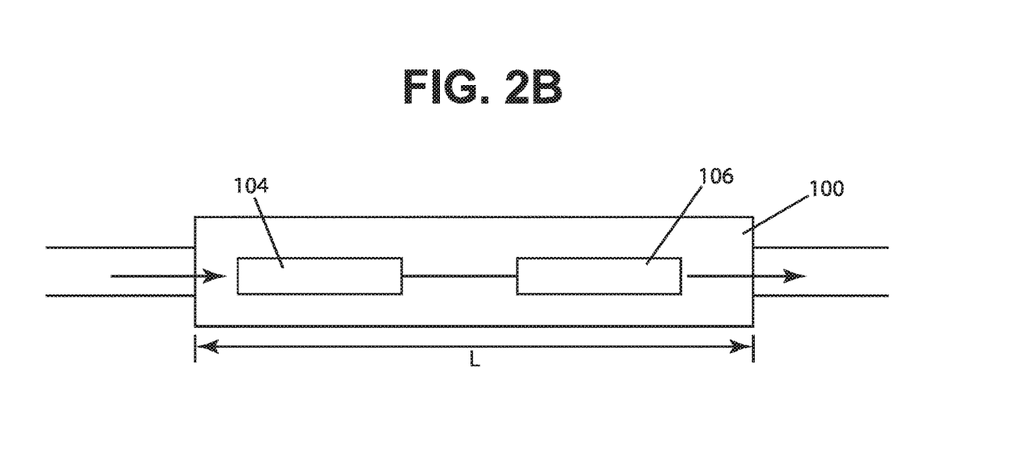

FIGS. 2A and 2B illustrate the top and side cut-away views of valve 100 which can include a setting device 104 to adjust the valve 100. In some examples, the settings can be changed under the influence of a directed magnetic field. Also, in an example, the valve 100 can have a plurality of predetermined settings corresponding to a plurality of predetermined rotational orientations of the setting device 104. In some examples, the plurality of settings comprises eight settings. It is to be understood that the valve 100 can be any settable, implantable valve, including a magnetically settable one. Further, an indicator 106 can be part of or in communication with the setting device 104 to provide information regarding the actual setting of the valve 100. Thus, as the setting device 104 is changed to change the flow parameters of the valve 100, the indicator 106 can reflect these changes, even in real time.

Figure 3:
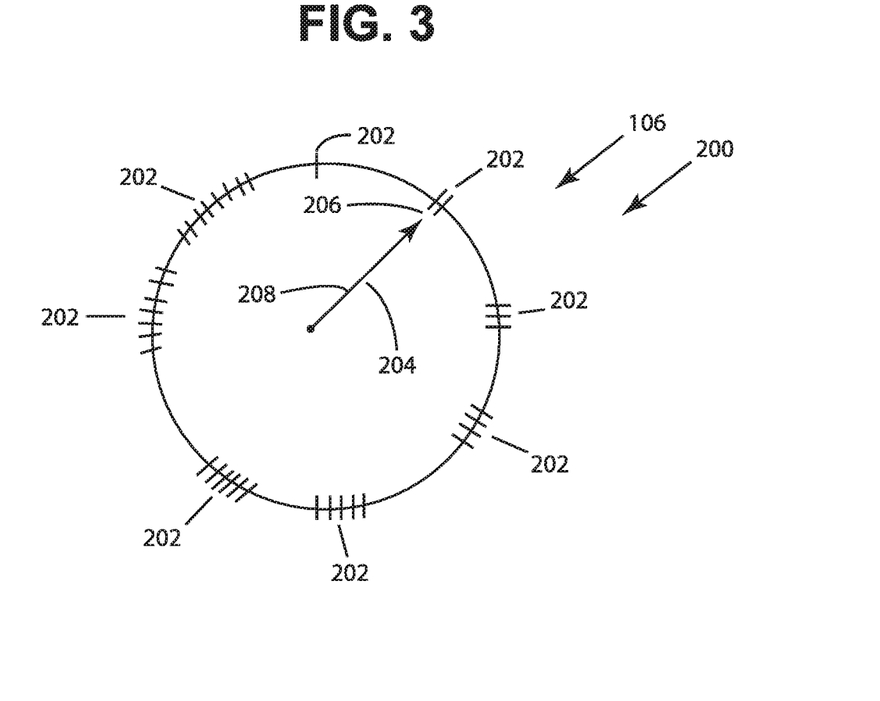
FIG. 3 is an example of an indicator of the present invention.

Examples of the invention use ultrasound technology to detect the position of the valve's setting. In one example, illustrated in FIG. 3, the indicator 106 can be selectively treated with ultrasound reflective materials 200. These materials reflect more ultrasound signal than any other feature of the valve 100 or the surrounding skin and more to increase the accuracy of the reading. The indicator 106 can be treated with ultrasound setting marks 202. Each mark 202 can indicate a valve setting. Each setting mark 202 can be a unique identifier or just one or a few marks 202. FIG. 3 illustrates the indicator 106 as a circular element, akin to a watch face, but it is known that any indicator 106 can be used by one of skill in the art. In the illustrated example, there are a number of elements that make up the setting mark 202 and each identify a numerical position on the indicator (i.e. 1=|; 2=||; 3=|||; 4=||||), alternately, the setting mark 202 can be the numeral itself. In another example, just the first setting mark 202a can differ from the rest and there is a protocol to reading the remaining marks (e.g. the setting mark to the left of the first setting mark is setting 8, and the one to the right is setting 2, etc.) (see, FIG. 4 as an example).

Figure 4:
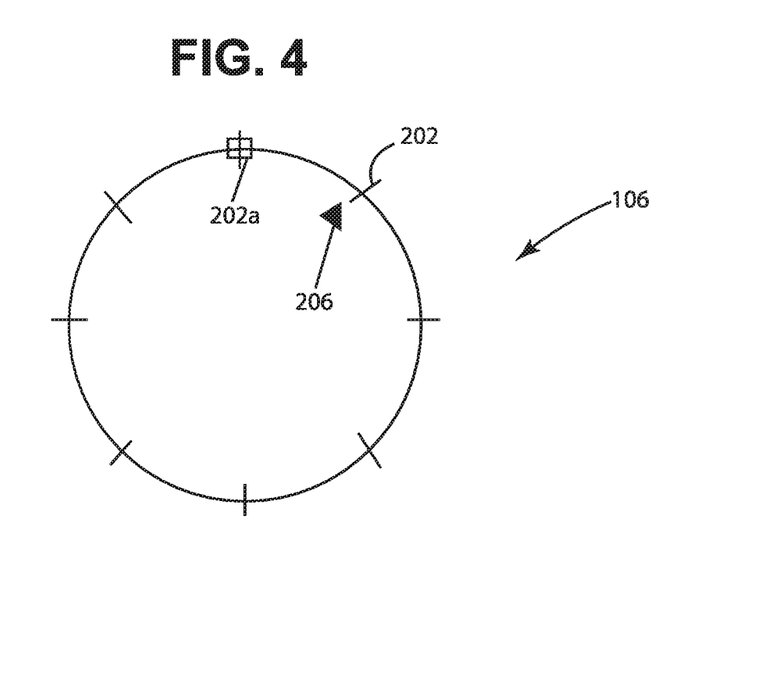
FIG. 4 illustrates an example representation of the indicator as seen by ultrasound.

The indicator 106 can also include an identifier 204. The identifier 204 identifies the setting of the valve 100, in this example, by its position relative to the setting marks 202. The identifier 204 can also be selectively treated with ultrasound reflective materials to assist in determining its position. For example, just the tip 206 closest to the setting marks 202 or the entire hand 208 can be treated. Note that the changing of the setting device 104 can alter the position of either the setting marks 202 or the identifier 204, as either can move relative to the other. FIG. 4 illustrates the indicator 106 of above example as seen by just ultrasound echo. Due to the selective treatments, only the setting marks 202 and tip 206 of the identifier 204 are visible.

Figure 5:
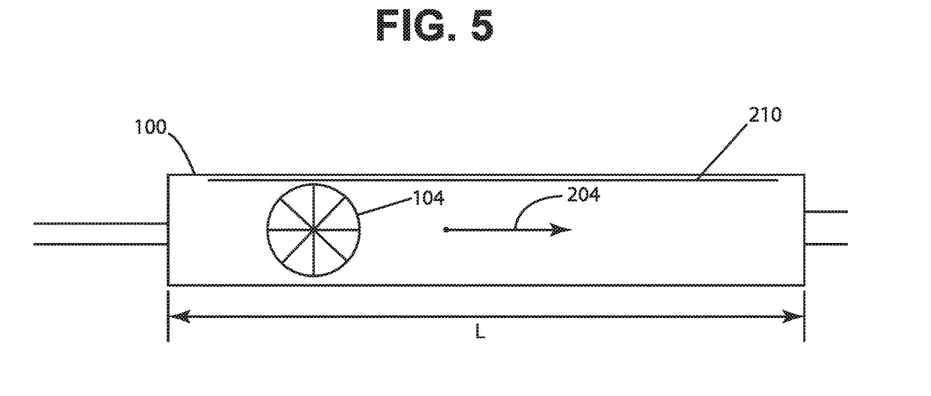
FIG. 5 illustrates an example of a valve with an axis mark and identifier of the present invention.
Figure 6:
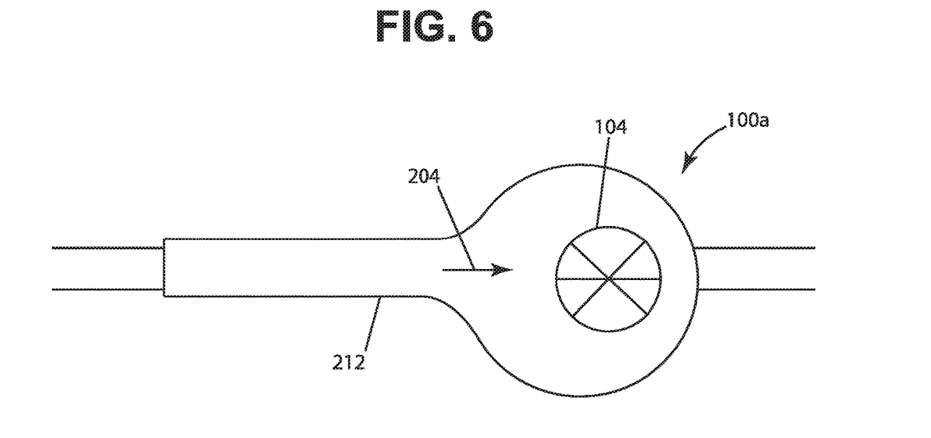
FIG. 6 illustrates another example of a valve of the present invention.

Another example of indicating the setting of the valve 100 can be based on the orientation of the valve 100 itself relative to the position of the identifier 204. FIG. 5 illustrates an example of an ultrasound axis mark 210 parallel to the long axis L of the valve 100. Here once an operator understands the orientation of the valve using the ultrasound axis mark 210, the setting noted by the identifier 204 can be discerned based on the relative position of the two. Further to the example of using the orientation of the valve 100, FIG. 6 illustrates an example where a portion or the entire valve 100a is coated with an ultrasound outline mark 212. In this example, the valve 100a is not symmetric and the outline of the valve 100a can be selectively treated with ultrasound reflective materials to form the outline mark 212. Again, once an operator understands the position of the valve 100a from its asymmetric shape, the position of the identifier 204 relative to the shape as defined by the outline mark 212 can be discerned, and thus the valve setting determined. Further, in certain examples, the outline mark 212 does not have to enclose the entire area and/or perimeter of the valve 100a, the mark or marks 212 need, at a minimum, to identify the non-symmetric shape so a user can determine valve orientation.

Turning now to "ultrasound" and selectively treating elements of the invention with ultrasound reflective materials. Ultrasound herein in examples is used in its broadest meaning of the use of sound waves to determine subcutaneous elements. This determination can be reported to the user as visual or non-visual indicators. In the visual sense, a typical ultrasound can produce images in real time of subcutaneous elements in accordance with their reflective properties. Non-visual indications can also be encompassed in examples of the invention. Here, either an audio cue can be used determine the setting, or a processor can interpret the ultrasound results and report back to the user just information regarding the setting of the valve.

Selectively treating elements of the invention with ultrasound reflective materials indicates that the element is at least partially or fully made from or treated with materials or surface features that increase the ability of the material to reflect ultrasound waves. This can be by a selection of materials for both the valve 100 and the elements to be ultrasonically identified. Alternately, small air bubbles can be entrained into plastic elements to exploit the known difference in reflection between solids and air. Furthermore, other examples can utilize distinct surface features, like properly sized and spaced pits, to change the reflectance. For example, other ultrasound reflection enhancing treatments may consist of mechanical corner cube indentations on the surface of the indicator 106, which direct more of the energy back to the source. Additionally, spacing, banding, or striations between marks can also be used as unique identifiers. In addition, any means, materials, or methods known to one of ordinary skill to improve ultrasound wave reflection are contemplated in these examples.

Figure 7A:
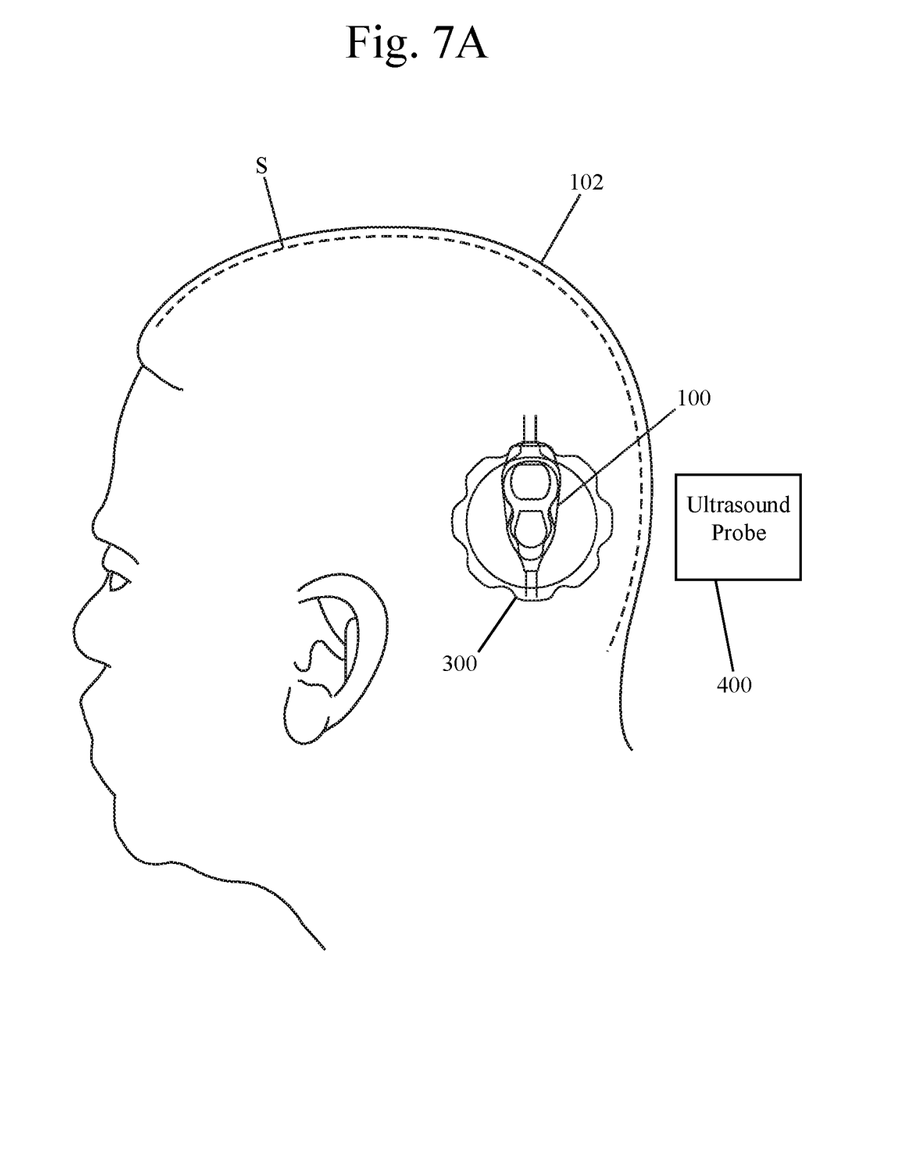
FIG. 7A illustrates an example of the valve adjustment tool and ultrasound probe in use.

Addressing the method of using the invention, since the identification of the valve setting is performed by ultrasound, the position can be determined in real time and/or contemporaneously with the setting of the valve. Real time determination can happen as soon as the medical professional removes a valve adjusting tool 300, used to alter the valve's settings. Once removed an ultrasound probe 400 can be placed over the valve 100 to read the image of the location of the indicator 104, identifier 206 and/or the marks 202, 210, 212. Even more immediate feedback can be provided further to examples of the invention. FIG. 7A illustrates the patent with the installed valve 100. Here, the adjusting tool 300 can be in place over the valve 100 and an ultrasound probe 400 can be separately placed nearby. The probe 400 can read the identifier 206 as it is being moved by the movement of the adjusting tool 300. In this example, the identifying features 104, 206, 202, 210, 212 can be configured to be read perpendicular or oblique to the top surface of the valve 100. As the adjusting tool 300 is set on top of the valve 100, the probe 400 can come along side and identify the markings sidelong.

Figure 7B:
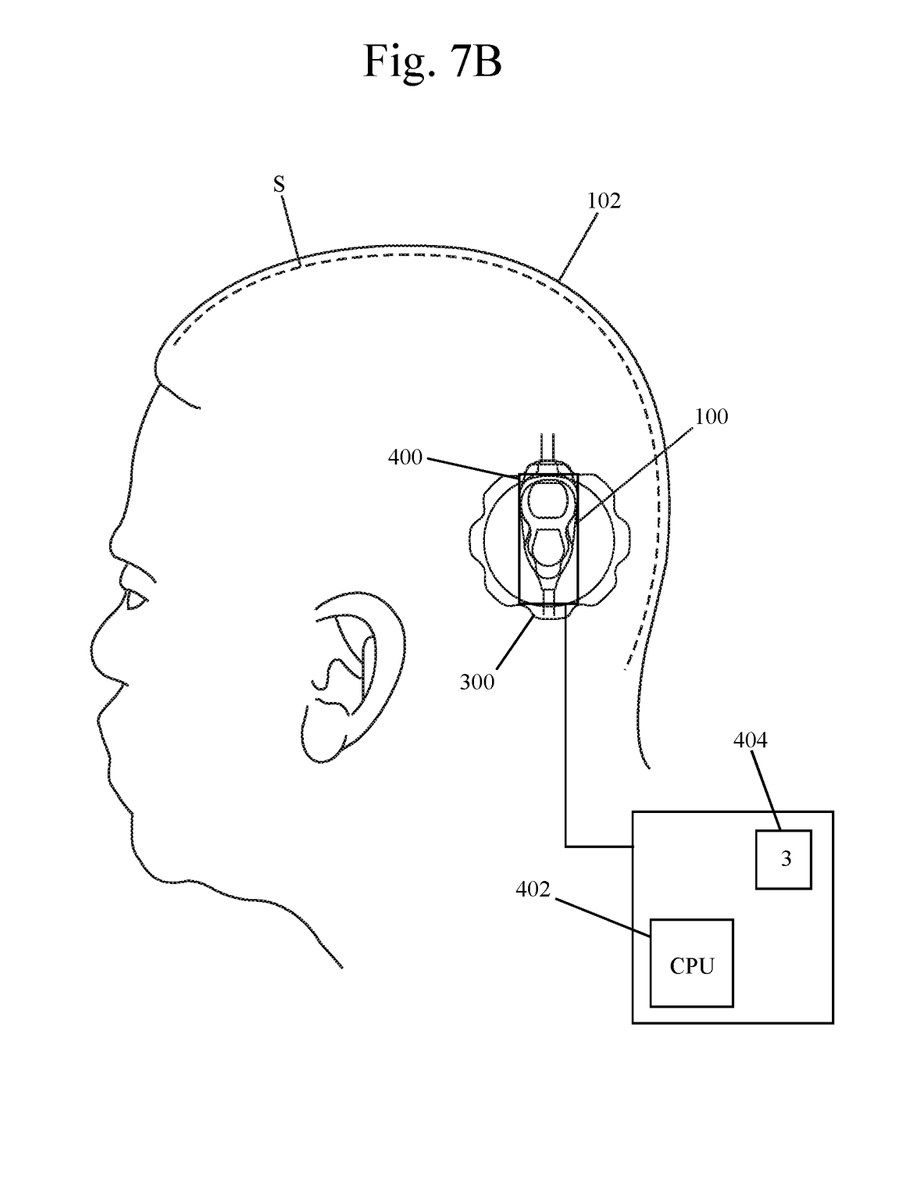
FIG. 7B illustrates an example of the valve adjustment tool with ultrasound probe in use.

FIG. 7B illustrates a similar concept that can correct for the sidelong reading. In this example the ultrasonic probe 400 is built into the adjusting tool 300. This example allows the combination tool/probe 300, 400 to take a top down reading and adjust the valve simultaneously. This example can also simplify locating the valve 100 under the patient's skin 102. Normally, to locate the valve 100 under the skin 102, the user typically palpates the skin 102 until she can feel the valve 100. Now the medical professional can run the combination tool/probe 300, 400 over the patient's skin until an identifying feature 104, 206, 202, 210, 212 can be located. As noted above, the probe 400 can also include a processor 402 and a display 404 to provide real-time results from the probe 400. The processor 402 can interpret the information from the probe 400 and display 404 either an image or just a valve setting. Alternately, the display 404 can be speaker and provide audio information regarding the valve setting.

Figure 8:
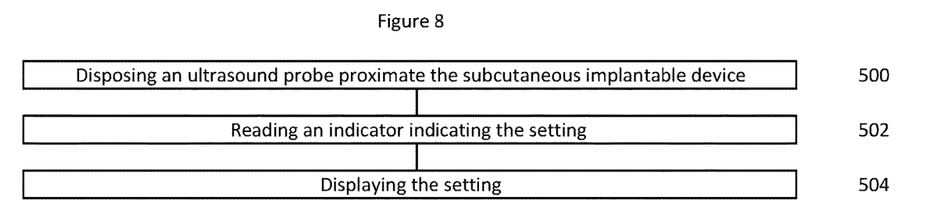
FIG. 8 illustrates a flow chart of an example of a method of the present invention.

FIG. 8 illustrates an example of a method of the present invention. The method includes determining a setting of a subcutaneous implantable device (e.g. implanted valve 100) having one or more adjustable settings. The user or medical professional can dispose the ultrasound probe 400 proximate the subcutaneous implantable device 100 (step 500). The probe can read the indicator 106 indicating the setting of the one or more adjustable settings based on an ultrasound reflection enhancement 200 on the indicator 106 (step 502). The read setting can be displayed on the display 404 (step 504).

Figure 9:
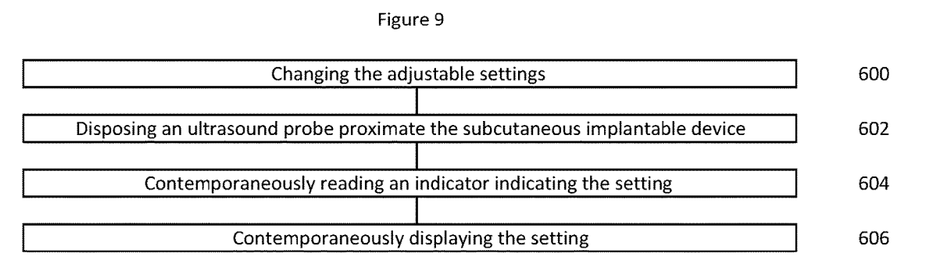
FIG. 9 illustrates a flow chart of an example of a contemporaneous method of the present invention.

FIG. 9 is an example of the method when the adjusting tool 300 and the probe 400 are used in tandem. Here one or more adjustable settings of the valve 100 are changed the using a adjusting tool 300 (step 600) and the user or medical professional can dispose the ultrasound probe 400 proximate the subcutaneous implantable device 100 (step 602). Examples of this step can be the probe and tool 400, 300 are a single device, or the indicator 106 can be configured to allow for sidelong indications and reading. Then the readings of the indicator 106 indicating the setting of the one or more adjustable settings based on an ultrasound reflection enhancement 200 on the indicator 106 (step 604) can happen contemporaneously with the adjustment, or as fast at the indicator 106 can calibrate to the newly adjusted setting. With the contemporaneous reading the setting can also be displayed contemporaneously, or in real time (step 606).

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A subcutaneous implantable device having one or more adjustable settings, comprising:
   a body of the subcutaneous implantable device constructed with ultrasound reflective material;
   a setting device positioned on the body and configured to selectively change between the one or more adjustable settings associated with fluid flow parameters of the device; and
   an indicator positioned on the body and indicating each particular setting of the one or more adjustable settings and comprising an ultrasound reflection enhancement comprising ultrasound reflective material wherein the implantable device is configured to operate with an ultrasound probe to take real-time readings of the one or more adjustable settings.

2. The subcutaneous implantable device of claim 1, wherein the ultrasound reflective material is configured to reflect more ultrasound signal than any other feature of the subcutaneous implantable device or the surrounding skin and increase accuracy of the readings.

3. The subcutaneous implantable device of claim 1, wherein the indicator further comprises:

one or more setting marks, each mark identifying each particular setting of the one or more adjustable settings; and an identifier identifying each mark as set by the setting device, wherein the one or more setting marks and the identifier comprise the ultrasound reflection enhancement.

4. The subcutaneous implantable device of claim 1, further comprising:

an orientation axis determining a positional orientation of the device as implanted; and an axis identifier disposed along at least a portion of the orientation axis and comprising an ultrasound reflection enhancement, wherein the indicator indicates the particular settings in relation to the axis identifier.

5. The subcutaneous implantable device of claim 1, further comprising:

the body enclosing at least the setting device;

a perimeter outlining the body; and an outline mark along at least a portion of the perimeter and comprising an ultrasound reflection enhancement, wherein the indicator indicates the particular settings in relation to the outline mark.

6. The subcutaneous implantable device of claim 1, wherein the body is asymmetric.

7. An adjustment tool for a subcutaneous implantable device having one or more adjustable settings, comprising:

a body of the subcutaneous implantable device constructed with ultrasound reflective material configured to reflect more ultrasound signal than any other feature of the subcutaneous implantable device;

an adjusting tool configured to change the one or more adjustable settings;

an ultrasound probe configured with the adjusting tool to take real-time readings of the one or more adjustable settings associated with fluid flow parameters of the implantable device as the adjustment tool makes the change; and a display linked to the probe and indicating the setting.

8. The adjustment tool of claim 7, further comprising:

a subcutaneous implantable device having one or more adjustable settings, comprising:

a setting device configured to selectively change between the one or more adjustable settings; and an indicator indicating each particular setting of the one or more adjustable settings and comprising an ultrasound reflection enhancement.

9. The adjustment tool of claim 8, wherein the indicator of the subcutaneous implantable device further comprises:

one or more setting marks, each mark identifying each particular setting of the one or more adjustable settings; and an identifier identifying each mark as set by the setting device, wherein the one or more setting marks and the identifier comprise the ultrasound reflection enhancement.

10. The adjustment tool of claim 8, wherein the indicator of the subcutaneous implantable device consists of eight setting marks, each mark identifying each particular setting of the one or more adjustable settings; and an identifier identifying each mark as set by the setting device, wherein the setting marks and the identifier comprise the ultrasound reflection enhancement comprising materials that reflect more ultrasound signal than any other feature of the subcutaneous implantable device or the surrounding skin and increase accuracy of the readings.

11. A method of determining a setting of a subcutaneous implantable device having one or more adjustable settings, comprising the steps of:

disposing an ultrasound probe proximate the subcutaneous implantable device, the subcutaneous implantable device comprising: a body having ultrasound reflective material; a setting device positioned on the body and configured to selectively change between the one or more adjustable settings associated with fluid flow parameters of the implantable device; and an indicator positioned on the body and indicating each particular setting of the one or more adjustable settings and comprising an ultrasound reflection enhancement comprising ultrasound reflective material;

reading the indicator indicating the setting of the one or more adjustable settings based on the ultrasound reflection enhancement on the indicator; and displaying the setting.

12. The method of claim 11, further comprising the step of:

changing the one or more adjustable settings using an adjusting tool, wherein the reading and displaying steps are performed contemporaneous with the changing step.

* * * * *